(12) United States Patent
Adametz et al.

(10) Patent No.: US 11,351,333 B2
(45) Date of Patent: Jun. 7, 2022

(54) VENTILATOR WITH SWITCHING VALVE

(71) Applicant: Loewenstein Medical Technology S.A., Luxembourg (LU)

(72) Inventors: Benjamin Adametz, Hamburg (DE); Christof Goebel, Hamburg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 548 days.

(21) Appl. No.: 16/293,815

(22) Filed: Mar. 6, 2019

(65) Prior Publication Data

US 2019/0275283 A1  Sep. 12, 2019

(30) Foreign Application Priority Data

Mar. 8, 2018 (DE) .................. 102018001888.2

(51) Int. Cl.
*A61M 16/20* (2006.01)
*A61M 16/00* (2006.01)
*A61M 16/12* (2006.01)
*A61M 16/08* (2006.01)
*A61M 16/10* (2006.01)

(52) U.S. Cl.
CPC ...... *A61M 16/201* (2014.02); *A61M 16/0057* (2013.01); *A61M 16/022* (2017.08); *A61M 16/0883* (2014.02); *A61M 16/12* (2013.01); *A61M 16/208* (2013.01); *A61M 16/0003* (2014.02); *A61M 16/0066* (2013.01); *A61M 16/1005* (2014.02); *A61M 2016/0039* (2013.01); *A61M 2016/0042* (2013.01); *A61M 2202/0208* (2013.01); *A61M 2205/3334* (2013.01); *A61M 2205/75* (2013.01)

(58) Field of Classification Search
CPC ............ A61M 16/201; A61M 16/0057; A61M 16/0883; A61M 16/022; A61M 16/208; A61M 2205/3334; A61M 16/00
See application file for complete search history.

(56) References Cited

U.S. PATENT DOCUMENTS

| | | | | |
|---|---|---|---|---|
| 4,791,922 A * | 12/1988 | Lindsay-Scott | ... | A61M 16/0081 128/205.28 |
| 5,909,731 A | 6/1999 | O'Mahony | | |
| 8,893,718 B2 * | 11/2014 | Heinonen | ............. | A61M 16/22 128/205.24 |
| 2003/0145855 A1 * | 8/2003 | Fuhrman | ............... | A61M 16/10 128/204.18 |

(Continued)

FOREIGN PATENT DOCUMENTS

| | | |
|---|---|---|
| CN | 105617527 A | 6/2016 |
| CN | 107308531 A | 11/2017 |

(Continued)

*Primary Examiner* — Margaret M Luarca
(74) *Attorney, Agent, or Firm* — Abel Schillinger, LLP

(57) ABSTRACT

Disclosed is a ventilator with an apparatus input and an apparatus output and with an airway between the apparatus input and the apparatus output. A breathing gas drive, a non-return valve and a switching valve are arranged in the airway. The non-return valve prevents a flow of breathing gas in a direction from the apparatus output to the apparatus input and the switching valve enables at least temporarily a flow of breathing gas in a direction from the apparatus output to the apparatus input.

20 Claims, 7 Drawing Sheets

(56) References Cited

U.S. PATENT DOCUMENTS

| | | |
|---|---|---|
| 2010/0078017 A1 | 4/2010 | Andrieux |
| 2010/0319691 A1 | 12/2010 | Lurie |
| 2011/0197889 A1* | 8/2011 | Lahde ................. A61M 16/205 |
| | | 128/204.28 |
| 2012/0145156 A1 | 6/2012 | Lofaso |
| 2012/0145261 A1* | 6/2012 | Mashak .............. A61M 16/202 |
| | | 137/560 |
| 2013/0276789 A1 | 10/2013 | Garde |
| 2018/0221606 A1* | 8/2018 | Brandt .................. A61M 16/01 |

FOREIGN PATENT DOCUMENTS

| | | |
|---|---|---|
| DE | 102009025327 A1 | 3/2010 |
| GB | 2335604 A | 9/1999 |
| WO | 2012085792 A1 | 6/2012 |
| WO | 2017025178 A1 | 2/2017 |

* cited by examiner

VENTILATOR WITH SWITCHING VALVE

CROSS-REFERENCE TO RELATED APPLICATIONS

The present application claims priority under 35 U.S.C. § 119 of German Patent Application No. 102018001888.2 filed Mar. 8, 2018, the entire disclosure of which is expressly incorporated by reference herein.

BACKGROUND OF THE INVENTION

1. Field of the Invention

The present invention relates to a ventilator with an apparatus input and an apparatus output and with an airway between the apparatus input and the apparatus output, wherein a breathing gas drive, a non-return valve and a switching valve are arranged in the airway.

2. Discussion of Background Information

Ventilators are used for the therapy of respiratory disorders, and thus the ventilators can be used in non-invasive and invasive ventilation, both in and out of hospitals.

For the artificial respiration of patients, a ventilator can as a rule be used which has an inspiratory branch for the breathing gas flow and optionally a branch for the expiratory gas flow. The branch for the expiratory breathing gas flow enables the exhalation/expiration of a breathing gas through the patient, whilst the branch for the inspiratory gas flow provides the patient with the breathing gas.

With the ventilators known from the prior art there may arise both blockages/obstructions in the expiratory branch and also in the inspiratory branch of the ventilator.

A blockage/obstruction in the expiratory branch can be caused by way of example by the intake of material, such as by way of example medicaments or secretions.

Blockages/obstructions in the expiratory branch can prevent a patient from exhaling breathing gas.

A blockage/obstruction of the expiratory branch can lead by way of example to the airway pressure in the expiration not being able to drop to the intended pressure level, whereby a patient cannot breathe out. A stalling increased airway pressure in the airways of the patient can have harmful consequences. It can lead by way of example to a dangerous rise in the intrathoracic pressure, which leads to a reduced venous return, reduced cardiac output and finally to a drop in the arterial blood pressure.

In addition to the problems of a blockage/obstruction in the expiratory branch of the ventilator, there may also be a blockage/obstruction in the inspiratory branch of the ventilator. A blockage/obstruction in the inspiratory branch can be caused by way of example by a malfunction of the breathing gas drive. Blockages/obstructions in the inspiratory branch can prevent or at least impede the patients from breathing in.

The ventilators known from the prior art thus have the disadvantage that, even with existing safety devices, they are not sufficiently safeguarded against blockages, obstructions or malfunctions, so that inspiration and/or expiration of the breathing gas cannot be guaranteed.

In view of the foregoing it would be advantageous to have available a ventilator which ensures security of inspiration and/or expiration of breathing gas in the event of an obstruction/blockage of an inspiratory or expiratory branch of the ventilator.

SUMMARY OF THE INVENTION

The present invention provides a ventilator with at least one apparatus input and one apparatus output and with an airway between the apparatus input and apparatus output, wherein a breathing gas drive, a non-return valve and a switching valve are arranged in the airway. The airway usually is an inspiratory airway. The ventilator can optionally comprise at least one inspiratory airway and at least one expiratory airway. More typically, at least one non-return valve is arranged in at least one inspiratory airway. The non-return valve can be arranged between the apparatus input and the breathing gas drive. The non-return valve can alternatively be arranged between the breathing gas drive and the apparatus output. A breathing gas drive can be a blower or a pressure source, more particularly an oxygen or air pressure source.

According to the invention the non-return valve prevents a flow of breathing gas in a direction from the apparatus output to the apparatus input, and the switching valve enables at least temporarily a flow of breathing gas in the direction from the apparatus output to the apparatus input or to a separate apparatus opening. The separate apparatus opening can be here a second/separate apparatus input or a second/separate apparatus output. A switching valve can be electromechanical in design. A switching valve can be by way of example a pneumatic valve with a magnetic valve, or a bypass with a magnetic valve. A switching valve can be a 3/2-way valve, a pneumatic valve or a diaphragm valve.

As a rule, expirated breathing gas from the patent can be discharged via an expiratory airway of the ventilator. A return of the breathing gas through the inspiratory airway can thus be prevented. The non-return valve prevents undesired contamination of the breathing gas drive from the non-purified breathing gas of the patient during normal operation of the ventilator. In the event of a blockage/obstruction of the expiratory airway the non-return valve can be reversed at least temporarily by the incorporated switching valve. This has the advantage that, in the event of a blockage of the expiratory airway, the breathing gas of the patient can be discharged via the inspiratory airway.

In one configuration a flowmeter is arranged between the non-return valve and the apparatus output. The flowmeter is set up to detect a flow or volume or a pressure of the breathing gas in the airway. The switching valve is set up so that it can be opened or closed based on the detected flow or volume or pressure of the breathing gas. This enables the switching valve to be switched in dependence on the volume or pressure of the breathing gas. Alternatively, the switching valve can be time-controlled or patient-triggered. The switching valve can be switched by way of example by a 3/2-way valve.

In another configuration the switching valve is arranged in a bypass around the non-return valve. The bypass can be designed open or closed. Closed means that the bypass opens into the airway from which it is branched off and then bypasses the non-return valve. The switching valve is as a rule arranged in the bypass. Open means that the bypass does not open into the airway from which it branches off. Rather an open bypass is an airway which can have by way of example a separate/second apparatus output. The open bypass as a rule branches off between the apparatus output and the breathing gas drive or the non-return valve, and opens in the separate/second apparatus output. Alternatively, the open bypass can branch off between the non-return valve and the breathing gas drive, and open into the second/separate apparatus output. A flowmeter can be arranged in the open bypass. The flowmeter is usually arranged between the second/separate apparatus output and the bypass. A separate switching valve can be arranged in the open bypass. The switching valve can be switched time-controlled, patient-triggered or based on a flow or volume or pressure of the breathing gas detected by the flowmeter. The flowmeter is as a rule arranged between the switching valve and the common apparatus output. The open bypass can optionally be formed additionally to a closed bypass. The open bypass has the advantage that breathing gas exhaled by the patient can be discharged to the atmosphere via the separate/second apparatus output.

In a further design of the invention the at least one switching valve forms a bypass around the non-return valve. By designing the closed bypass around the non-return valve, it is possible to bypass the non-return valve in such a way that the breathing gas is introduced round the non-return valve into the same airway from which it was branched off. The at least one switching valve optionally forms an open bypass around the non-return valve. In the case of the open-type bypass, breathing gas can, in the event of a blockage/obstruction of the inspiratory airway, be discharged via the open bypass past the non-return valve through a separate apparatus output.

In one configuration the at least one switching valve is set up to open and/or close the bypass, wherein the switching valve is set up so that it can be switched automatically or actively. Usually, the switching valve is set up to open or close automatically, based on the detected flow or volume or pressure of the breathing gas. By way of example the switching valve opens when the flowmeter detects a higher pressure over a certain period of time.

In another configuration the breathing gas drive is arranged between the apparatus input and the non-return valve and is set up to convey breathing gas in the direction of the non-return valve and the apparatus output. The arrangement of the breathing gas drive defines a suction side and a pressure side in the ventilator. The suction side is the side in the gas flow direction upstream of the breathing gas drive. The pressure side is the side downstream of the breathing gas drive in the gas flow direction. By arranging the breathing gas drive directly behind the apparatus input, the non-return valve, the switching valve and the flow meter are located on the pressure side of the ventilator.

In one configuration according to the invention, the bypass branches off to the switching valve between the breathing gas drive and the non-return valve and opens back again into the airway between the non-return valve and the apparatus output. Through this arrangement, the breathing gas drive is protected during normal operation of the ventilator against undesired contamination through returning breathing gas.

In an alternative configuration of the invention the breathing gas drive is arranged between the non-return valve and the apparatus output and is set up to convey breathing gas towards the apparatus output. By arranging the breathing gas drive between the non-return valve and the apparatus output, the non-return valve and the switching valve are located on the suction side of the ventilator.

In a further development of the alternative configuration of the invention the bypass branches off to the switching valve between the apparatus input and the non-return valve, and opens back again into the airway between the non-return valve and the breathing gas drive. This has the advantage that the non-return valve can be bypassed. With an arrangement of this kind the switching valve and the non-return valve are moreover arranged on the suction side of the ventilator.

In a further configuration, in addition to the bypass, a second airway is formed which comprises a second apparatus input and at least one non-return valve, and opens in front of the common apparatus output into the first airway. More typically, the second airway is a separate inspiratory airway which is set up to provide, in the event of a blockage/obstruction of the inspiratory airway, a separate airway via which breathing gas can be inspirated. The second inspiratory airway can comprise a separate breathing gas drive. By way of example the breathing gas drive is arranged between the second apparatus input and the non-return valve of the second airway. Furthermore, the second airway can comprise a separate flowmeter which is set up to detect the flow or volume or pressure of the breathing gas in the second airway.

In a further configuration according to the invention, an airway is included for an expiratory gas flow which comprises an expiratory apparatus input and an expiratory apparatus output.

The airway for an expiratory gas flow is set up to discharge the breathing gas of the patient. The expiratory apparatus input is then arranged as a rule close to the patient whilst the expiratory apparatus output is formed away from the patient. The airway for the expiratory gas is set up to discharge the breathing gas of the patient at the expiratory apparatus output and thus to enable the patient to breathe out.

In a further development the airway leads from the expiratory apparatus input to the expiratory apparatus output, and a switching valve and a flowmeter are arranged in the airway. The flowmeter is arranged as a rule between the expiratory apparatus output and the switching valve. The switching valve is as a rule set up so that it can be switched based on a fixed time interval or by patient trigger. Alternatively, the switching valve can be switched based on the flow or volume or pressure of the breathing gas as measured by the flowmeter. The flowmeter which is arranged between the expiratory apparatus output and the switching valve is typically set up to detect the flow or volume or the pressure of the breathing gas and to enable feedback at the ventilator about the breathing gas discharged by the patient.

In a further development a separate expiratory airway with a switching valve and a flowmeter runs between the expiratory apparatus input and the switching valve to a separate apparatus output. The separate expiratory airway is set up to discharge the breathing gas of the patient, by way of example in the event of a blockage/obstruction of the expiratory airway. The flowmeter which is arranged between the expiratory apparatus output and the switching valve is typically set up to detect the flow or volume or the pressure of the breathing gas and to enable feedback about the breathing gas which is discharged by the patient.

In one configuration a tube system is adapted to the apparatus output and leads with a first branch to a patient interface and, in front of the patient interface, with a second branch to the expiratory apparatus input for expiratory breathing gas. The tube system is optionally a single-tube system. Alternatively, a tube system can be adapted to the apparatus output in the form of a leakage tube system. The patient interface is connected by the tube system to at least one inspiratory airway. The patient interface is optionally connected by the tube system to at least one inspiratory airway and at least one expiratory airway.

In a further configuration the non-return valve prevents the flow of breathing gas in a direction from the apparatus output to the apparatus input, and the switching valve enables at least temporarily a flow of breathing gas in a direction from the apparatus output to the apparatus input, wherein the switching valve is arranged in a bypass around the non-return valve, wherein the bypass branches off to the switching valve between the breathing gas drive and the non-return valve, and opens back again into the airway between the non-return valve and the apparatus output.

In a further development of the invention the ventilator comprises a second inspiratory airway, which comprises a separate apparatus input and a further non-return valve, wherein the second inspiratory airway is set up to draw in a breathing gas through the separate apparatus input and convey it towards the apparatus output.

In a further development, the switching valve is arranged in the bypass, wherein the bypass is formed as an open bypass which comprises a separate apparatus output, wherein the open bypass branches off from the inspiratory airway between the non-return valve and the apparatus output, and opens into the separate apparatus output.

In a further development of the invention the switching valve is arranged in the bypass, wherein the bypass is formed as an open bypass which comprises a separate apparatus output, wherein the open bypass branches off from the inspiratory airway between the non-return valve and the apparatus output, and opens into the separate apparatus output, wherein the inspiratory airway comprises at least one further valve.

In another further development, the switching valve is arranged in the bypass, wherein the bypass is formed as an open bypass which comprises a separate apparatus output, wherein the open bypass branches off from the inspiratory airway between the non-return valve and the apparatus output, and opens in the separate apparatus output, wherein at least one flowmeter is arranged in the open bypass.

The present invention further provides a ventilator with at least one apparatus input and one apparatus output and with an airway between the apparatus input and apparatus output, wherein a breathing gas drive, a non-return valve and a switching valve are arranged in the airway. The ventilator comprises a second inspiratory airway which comprises a separate apparatus input and a further non-return valve, wherein the second inspiratory airway is set up to draw in breathing gas in through the separate apparatus input and convey it towards the apparatus output.

The present invention further provides a ventilator with at least one apparatus input and an apparatus output and with an airway between the apparatus input and apparatus output, wherein a breathing gas drive, a non-return valve and a switching valve are arranged in the airway. The switching valve is arranged in a bypass, wherein the bypass is designed as an open bypass which comprises a separate apparatus output, wherein the open bypass branches off from the inspiratory airway between the non-return valve and the apparatus output, and opens into the separate apparatus output.

In one configuration the switching valve is arranged in the bypass wherein the bypass is designed as an open bypass which comprises a separate apparatus output, wherein the open bypass branches off from the inspiratory airway between the non-return valve and the apparatus output and opens into the separate apparatus output, wherein the inspiratory airway comprises at least one further valve.

In a further configuration the switching valve is arranged in the bypass, wherein the bypass is designed as an open bypass which comprises a separate apparatus output, wherein the open bypass branches off from the inspiratory airway between the non-return valve and the apparatus output, and opens in the separate apparatus output, wherein at least one flowmeter is arranged in the open bypass.

The present invention further provides a ventilator with at least one apparatus input and an apparatus output and with an airway between the apparatus input and the apparatus output, wherein a breathing gas drive, a non-return valve and a switching valve are arranged in the airway. The switching valve is arranged in a bypass, wherein the bypass is designed as an open bypass, which comprises a separate apparatus output, wherein the open bypass branches off from the inspiratory airway between the non-return valve and the apparatus output, and opens in the separate apparatus output, wherein the inspiratory airway comprises at least one further valve and a flowmeter, wherein the flowmeter is arranged between the breathing gas drive and the non-return valve.

BRIEF DESCRIPTION OF THE DRAWINGS

Preferred exemplary embodiments of the invention will now be explained below in further detail with reference to severely simplified diagrammatic illustrations. In the drawings.

In the figures the same structural elements are each provided with the same reference numerals.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
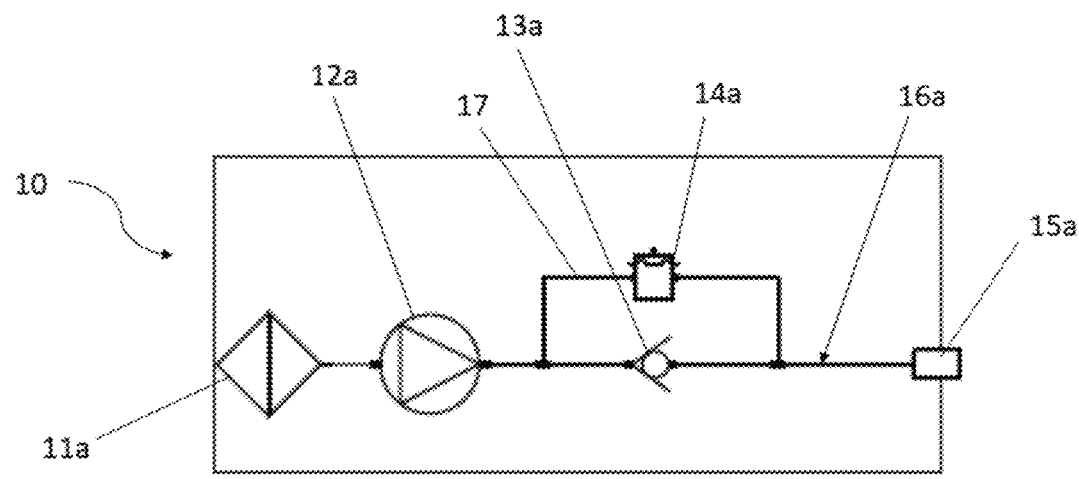
FIG. 1 shows a diagrammatic structure of an embodiment of a ventilator according to the invention with an inspiratory airway with a bypass around a non-return valve.

FIG. 1 shows a diagrammatic structure of an embodiment of a ventilator 10 according to the invention with an inspiratory airway 16a with a bypass 17 and the non-return valve 13a. The inspiratory airway 16a comprises an apparatus input 11a and an apparatus output 15a. The apparatus output 15a is arranged here close to the patient and the apparatus input 11a is arranged away from the patient. The airway 16a extends from the apparatus input 11a to the apparatus output 15a. The airway 16a comprises a breathing gas drive 12a, a non-return valve 13a and a switching valve 14a. The switching valve 14a is arranged in a bypass 17 around the non-return valve 13a. The bypass 17 branches off between the breathing gas drive 12a and the non-return valve 13a and opens back into the inspiratory airway 16a between the non-return valve 13a and the apparatus output 15a. The breathing gas drive 12a is arranged between the apparatus input 11a and the non-return valve 13a. Breathing gas can be returned in the direction of the apparatus input 11a via the switching valve 14a arranged in the bypass 17, whereby the non-return valve 13a is bypassed.

Figure 2:
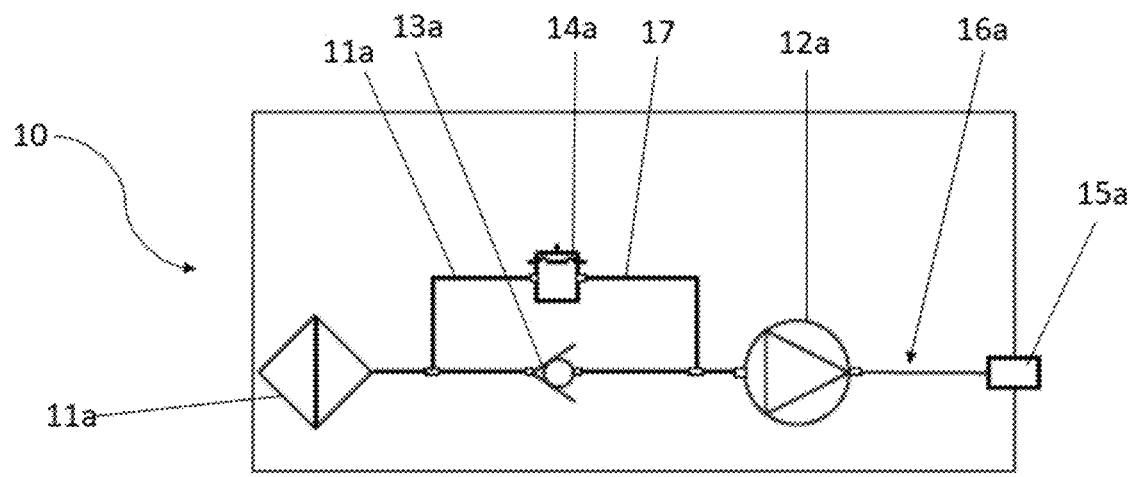
FIG. 2 shows an alternative arrangement of the embodiment of the ventilator according to the invention shown in FIG. 1, with the inspiratory airway with the bypass around a non-return valve.

FIG. 2 shows an alternative arrangement of the embodiment of the ventilator 10 according to the invention shown in FIG. 1, with the inspiratory airway 16a with the bypass 17 around the non-return valve 13a. The inspiratory airway 16a comprises the apparatus input 11a and the apparatus output 15a. The airway 16a extends from the apparatus input 11a to the apparatus output 15a. The airway 16a comprises the non-return valve 13a, the breathing gas drive 12a and the switching valve 14a. The switching valve 14a is arranged in the bypass 17 around the non-return valve 13a. The bypass 17 in this alternative arrangement branches off between the apparatus input 11a and the non-return valve 13a, and opens back again into the inspiratory airway 16a between the non-return valve 13a and the breathing gas drive 12a. The breathing gas drive 12a is arranged between the non-return valve 13a and the apparatus output 15a. After it has passed the breathing gas drive 12a the breathing gas can be returned in the direction of the apparatus input 11a via the switching valve 14a which is arranged in the bypass 17.

Figure 3:
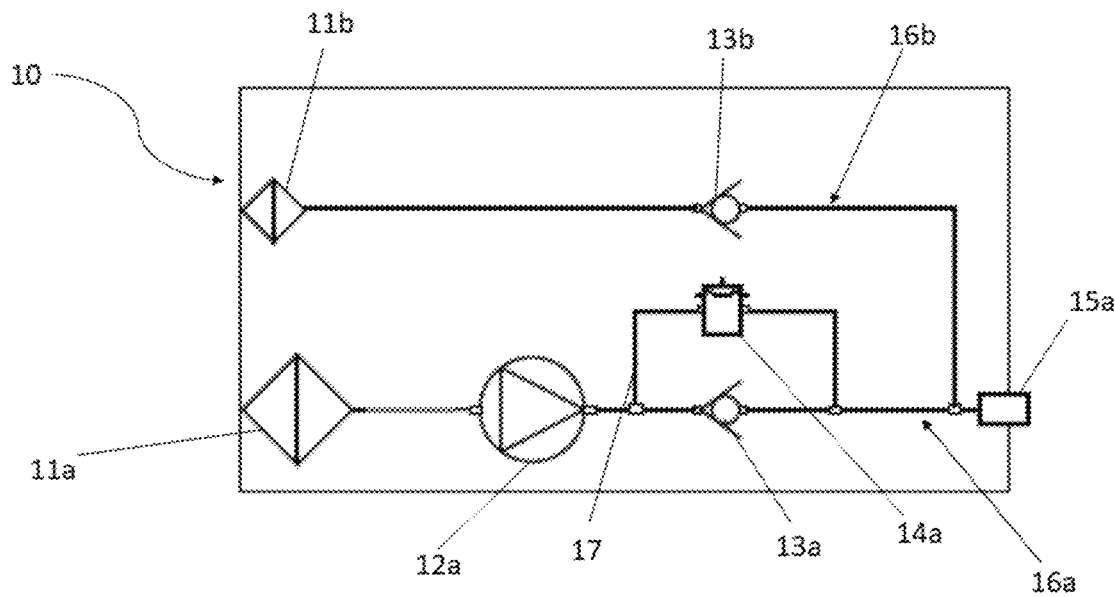
FIG. 3 shows a diagrammatic structure of a further embodiment of the ventilator according to the invention shown in FIG. 1, with the inspiratory airway with the bypass and a second inspiratory airway.

FIG. 3 shows a diagrammatic structure of a further embodiment of the ventilator 10 according to the invention, shown in FIG. 1, with the inspiratory airway 16a, the bypass 17 and a second inspiratory airway 16b. The inspiratory airway 16a extends from the apparatus input 11a to the apparatus output 15a. The inspiratory airway 16a comprises the breathing gas drive 12a, the non-return valve 14a and the switching valve 14a, wherein the switching valve 14a is arranged in the bypass 17 to bypass the non-return valve 13a. The embodiment of the ventilator 10 shown in FIG. 3 has a second inspiratory airway 16b which extends from a second apparatus input 11b to the common apparatus output 15a. The second inspiratory airway 16b opens into the inspiratory airway 16a between the non-return valve 13a and the common apparatus output 15a. The second inspiratory airway 16b can comprise a non-return valve 13b. In the event of a blockage/obstruction of the inspiratory airway 16a by way of example, breathing gas can be drawn in through the second inspiratory airway 16b via the separate apparatus input 11b and supplied to the patient. In addition, in the event of a blockage of an expiratory airway, breathing gas can be returned through the switching valve 14a whilst bypassing the non-return valve 13a, thereby enabling the patient to breathe out.

Figure 4:
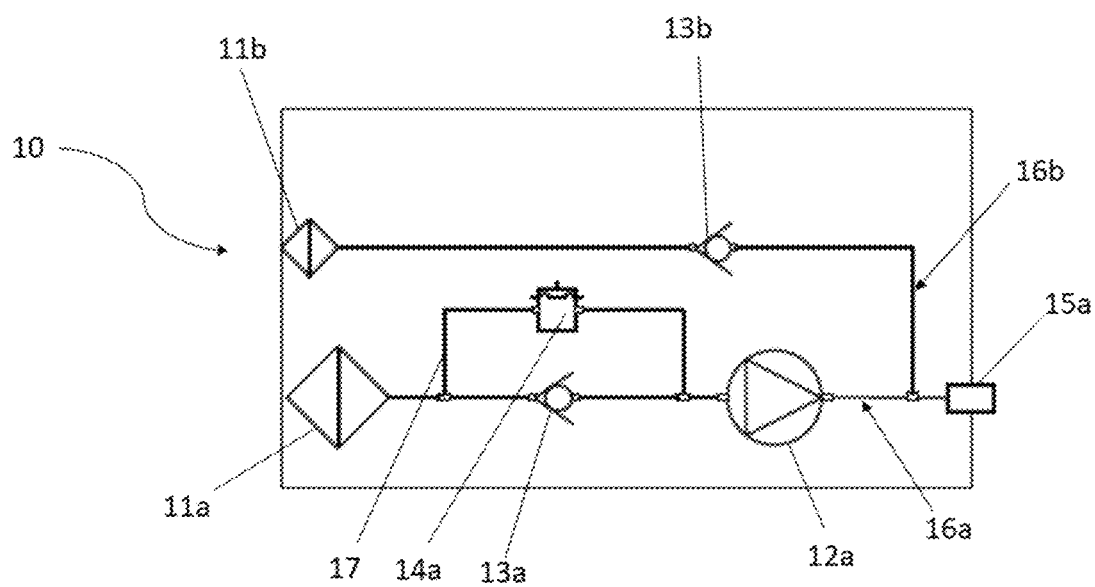
FIG. 4 shows an alternative arrangement of the embodiment, shown in FIG. 2, of the ventilator according to the invention shown in FIG. 1, with the inspiratory airway with the bypass and the second inspiratory airway.

FIG. 4 shows an alternative arrangement of the embodiment, shown in FIG. 2, of the ventilator 10 according to the invention, with the inspiratory airway 16a, the bypass 17 and the second inspiratory airway 16b. With this alternative embodiment the non-return valve 13a is arranged in the inspiratory airway 16a between the apparatus input 11a and the breathing gas drive 12a. The bypass 17, which is formed around the non-return valve 13a, branches off between the apparatus input 11a and the non-return valve 13a and opens back into the inspiratory airway 16a between the non-return valve 13a and the breathing gas drive 12a. The breathing gas drive 12a is arranged between the non-return valve 13a and the apparatus output 15a. The second inspiratory airway 16b opens into the inspiratory airway 16a between the breathing gas drive 12a and the common apparatus output 15a. The second inspiratory airway 16b can comprise a non-return valve 13b. Also with this embodiment, by way of example in the event of a blockage/obstruction of the inspiratory airway 16a, breathing gas can be drawn in through the second inspiratory airway 16b via the separate apparatus input 11b and supplied to the patient. In addition, likewise in the event of a blockage of an expiratory airway, breathing gas can be returned through the switching valve 14a by bypassing the non-return valve 13a, thereby enabling the patient to breathe out.

Figure 5:
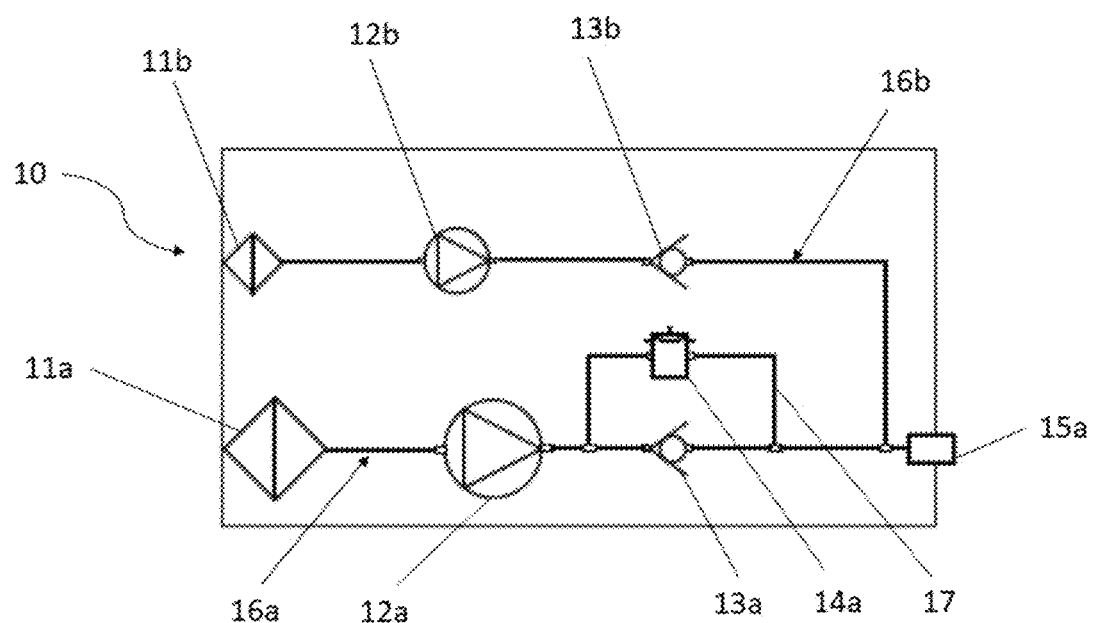
FIG. 5 shows an alternative arrangement of the embodiment, shown in FIG. 1 and FIG. 3, of the ventilator according to the invention, with the inspiratory airway with the bypass and the second inspiratory airway.

FIG. 5 shows an alternative arrangement of the embodiment, shown in FIGS. 1 and 3, of the ventilator 10 according to the invention, with the inspiratory airway 16a, the bypass 17 and the second inspiratory airway 16b.

The inspiratory airway 16a extends from the apparatus input 11a to the apparatus output 15a and comprises the breathing gas drive 12a, the non-return valve 14a and the switching valve 14a. The switching valve 14a is arranged in the bypass 17 around the non-return valve 13a. The bypass 17 is formed between the breathing gas drive 12a and the apparatus output 15a. The embodiment of the ventilator 10 shown in FIG. 5 likewise has the second inspiratory airway 16b which extends from the second apparatus input 11b to the common apparatus output 15a. The second inspiratory airway 16b opens into the inspiratory airway 16a between the non-return valve 13b and the common apparatus output 15a. The second inspiratory airway 16b comprises a non-return valve 13b and a breathing gas drive 12b, wherein the breathing gas drive 12b is arranged between the second apparatus input 11b and the non-return valve 13b. Also with this embodiment, by way of example in the event of a blockage/obstruction of the inspiratory airway 16a, breathing gas can be drawn in through the second inspiratory airway 16b via the separate apparatus input 11b and supplied to the patient. In addition, likewise in the event of a blockage of an expiratory airway, breathing gas can be returned through the switching valve 14a arranged in the bypass 17 so as to bypass the non-return valve 13a and enable the patient to breathe out.

Figure 6:
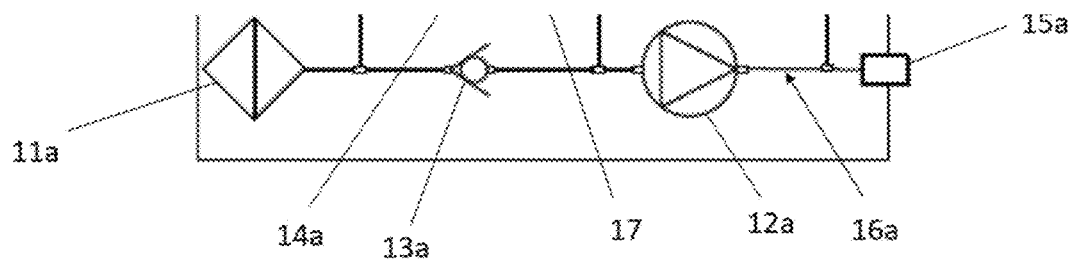
FIG. 6 shows an alternative arrangement of the embodiment, shown in FIG. 2 and FIG. 4, of the ventilator according to the invention, with the inspiratory airway with the bypass and the second inspiratory airway.

FIG. 6 shows an alternative arrangement of the embodiment of the ventilator 10 according to the invention shown in FIG. 2 and FIG. 4, with the inspiratory airway 16a, the bypass 17 and the second inspiratory airway 16b. The inspiratory airway 16a extends from the apparatus input 11a to the apparatus output 15a and comprises the non-return valve 13a, the switching valve 14a and the breathing gas drive 12a. The switching valve 14a is arranged in the bypass 17 to bypass the non-return valve 13b. The bypass 17 with the switching valve 14a is arranged between the apparatus input 11a and the breathing gas drive 12a. The embodiment of the ventilator 10 shown in FIG. 6 has the second inspiratory airway 16b which extends from a second apparatus input 11b to the common apparatus output 15a. The second inspiratory airway 16b opens into the inspiratory airway 16a between the breathing gas drive 12a and the common apparatus output 15a. The second inspiratory airway 16b comprises the non-return valve 13b and a breathing gas drive 12b, wherein the breathing gas drive 12b is arranged between the second apparatus input 11b and the non-return valve 13b.

Figure 7:
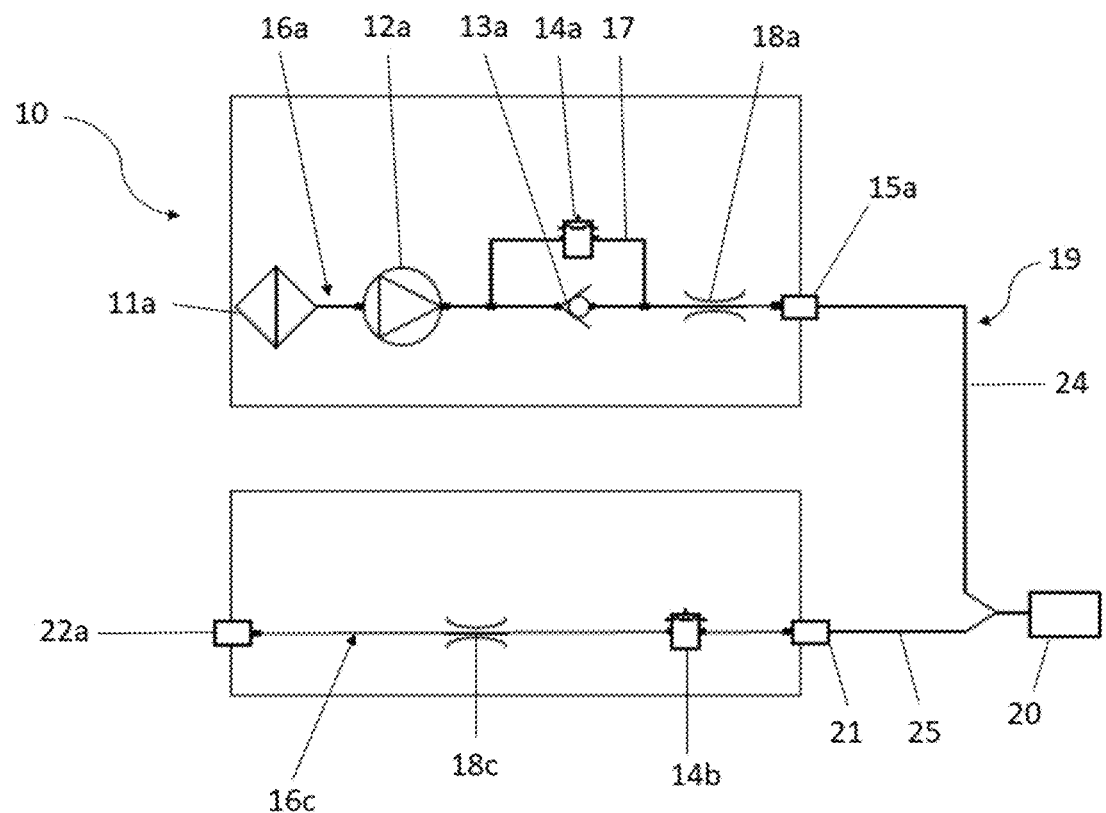
FIG. 7 shows a diagrammatic structure of an embodiment of the ventilator according to the invention with the inspiratory airway with the bypass and the expiratory airway.

FIG. 7 shows a diagrammatic structure of an embodiment of the ventilator 10 according to the invention with the inspiratory airway 16a with a bypass 17 and an expiratory airway 16c.

The inspiratory airway 16a extends from the apparatus input 11a towards the apparatus output 15a. The inspiratory airway 16a comprises here the breathing gas drive 12a, as well as the non-return valve 13a and the switching valve 14a, which is arranged in a bypass 17 around the non-return valve 13a, as well as a flowmeter 18a. The flowmeter 18a is arranged between the bypass 17 and the apparatus output 15a. A flow or volume or pressure of the breathing gas in the airway can be detected via the flowmeter 18a. With a predetermined volume or pressure of breathing gas over a predetermined period of time, the switching valve can be switched by way of example by means of a 3/2-way valve. The switching valve is as a rule set up and designed to set a PEEP (positive end-expiratory pressure) in the region of 0-20 hPa, preferably 0-15 hPa.

The expiratory airway 16c extends from an expiratory apparatus input 21 to the expiratory apparatus output 22a and comprises a switching valve 14b and a flowmeter 18c. The flowmeter 18c is then arranged between the expiratory apparatus output 22a and the switching valve 14b. The flowmeter 18c then serves to detect a flow or volume or a pressure of the breathing gas in the airway. Feedback on the volume of the breathing gas discharged by the patient can then be provided on the ventilator based on the values detected by the flowmeter 18c.

A tube system 19 comprising a first branch 24 and a second branch 25 is adapted to the apparatus output 15a. The first branch 24 leads from the apparatus output 15a to a patient interface 20. Before the patient interface 20 the tube system 19 leads with a second branch 25 to the expiratory apparatus input 21 for expiratory breathing gas. A patient interface 20 is connected via the tube system 19 to the inspiratory branch 16a and the expiratory branch 16c.

With the embodiment of the ventilator 10 illustrated in FIG. 7, breathing gas can be drawn in via the apparatus input 11a and guided via the breathing gas drive 12a via the non-return valve 13a in the direction of the apparatus output 15a. The breathing gas is passed further from the apparatus output 15a via the branch 24 of the adapted tube system 19 to the patient interface 20 via which a patient can breathe in the breathing gas. The exhaled air of the patient can be supplied to the airway 16c via the branch 25 of the adapted tube system 19 via the expiratory apparatus input 21. The breathing gas is guided via the expiratory airway 16c to the expiratory apparatus output 22a and discharged into the atmosphere. In the event of a blockage/obstruction of the expiratory airway 16c the breathing gas can be discharged in the inspiratory airway 16a by opening the switching valve 14a in the bypass 17.

Figure 8:
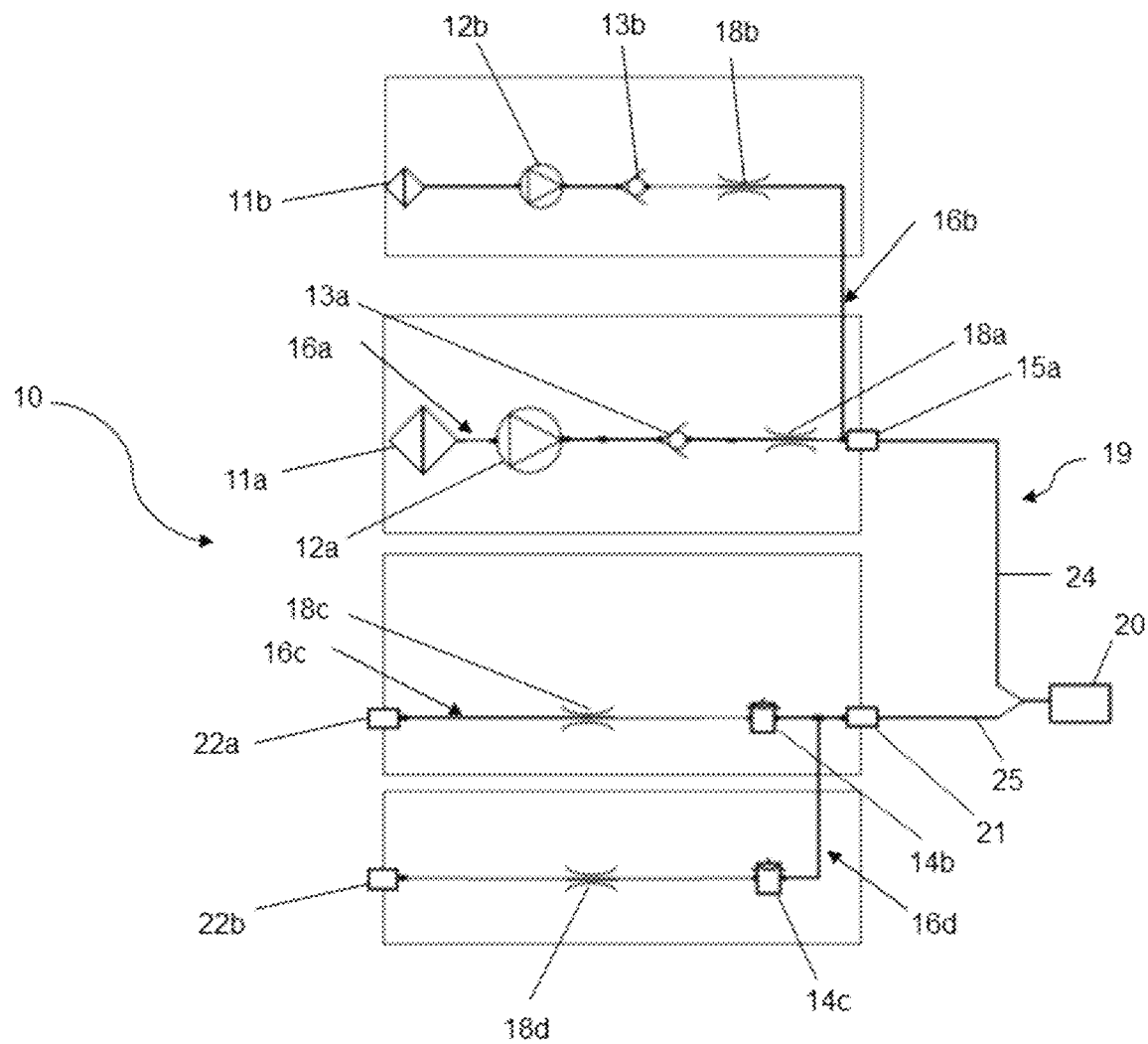
FIG. 8 shows a diagrammatic structure of a further embodiment of the ventilator according to the invention with the inspiratory airway and the second inspiratory airway as well as with an expiratory airway and a separate expiratory airway.

FIG. 8 shows a diagrammatic structure of a further embodiment of the ventilator 10 according to the invention with the first inspiratory airway 16a and the second inspiratory airway 16b, as well as with the expiratory airway 16c and a separate expiratory airway 16d.

The inspiratory airway 16a extends from the apparatus input 11a towards the apparatus output 15a. The inspiratory airway 16a comprises the breathing gas drive 12a, the non-return valve 13a as well as a flowmeter 18a. The flowmeter 18a is arranged between the non-return valve 13a and the apparatus output 15a. The flowmeter 18a detects a flow or a volume or a pressure of the breathing gas which is discharged via the inspiratory airway 16a to the patient.

The embodiment of the ventilator 10 shown in FIG. 8 comprises a second inspiratory airway 16b which extends from the second apparatus input 11b to the common apparatus output 15a. The second inspiratory airway 16b opens into the inspiratory airway 16a between the flowmeter and the common apparatus output 15a. The second inspiratory airway 16b can comprise the separate breathing gas drive 12b, the non-return valve 13b and a flowmeter 18b. The separate breathing gas drive 12b is arranged between the second apparatus input 11b and the non-return valve 13b. The flowmeter 18b can detect a volume or pressure of the inspiratory breathing gas in the airway 16b and send it to the ventilator 10. In the event of a blockage of the inspiratory airway 16a breathing gas can be drawn in via the second inspiratory airway 16b through the apparatus input 11b and supplied to the patient.

The embodiment of the ventilator 10 shown in FIG. 8 further comprises the expiratory airway 16c which extends from the expiratory apparatus input 21 to the expiratory apparatus output 22a and comprises the switching valve 14b and the flowmeter 18c. The flowmeter 18c is arranged between the expiratory apparatus output 22a and the switching valve 14b. The flowmeter 18c detects a volume and/or a pressure of the breathing gas which the patient is discharging. Breathing gas discharged by the patient can be removed via the expiratory airway 16c.

The flowmeters 18a, 18b, 18c and 18d can be set up to detect a flow or volume or a pressure of the breathing gas in the airway and to switch or open and close a switching valve based on this result or to supply feedback to the ventilator 10 about the flow or volume or the pressure of the breathing gas supplied to the patient or of the breathing gas discharged by the patient.

The embodiment of the ventilator 10 shown in FIG. 8 furthermore comprises a separate expiratory airway 16d. The separate expiratory airway 16d branches off from the expiratory airway 16c and extends towards a separate apparatus output 22b. The separate expiratory airway 16d comprises a switching valve 14c and a flowmeter 18d. The flowmeter 18d detects a flow or volume or a pressure of the breathing gas which the patient is discharging. In the event of a blockage/obstruction of the expiratory airway 16c breathing gas discharged by the patient can be discharged through the separate expiratory airway 16d.

A tube system 19 with a first branch 24 and a second branch 25 is adapted to the apparatus output 15a. The first branch 24 leads from the apparatus output 15a to a patient interface 20. Before the patient interface 20 the tube system 19 leads with the second branch 25 to the expiratory apparatus input 21 for expiratory breathing gas. The patient interface 20 is connected via the tube system 19 to the inspiratory airway 16a, the second inspiratory airway 16b, the expiratory airway 16c and the separate expiratory airway 16d.

Figure 9:
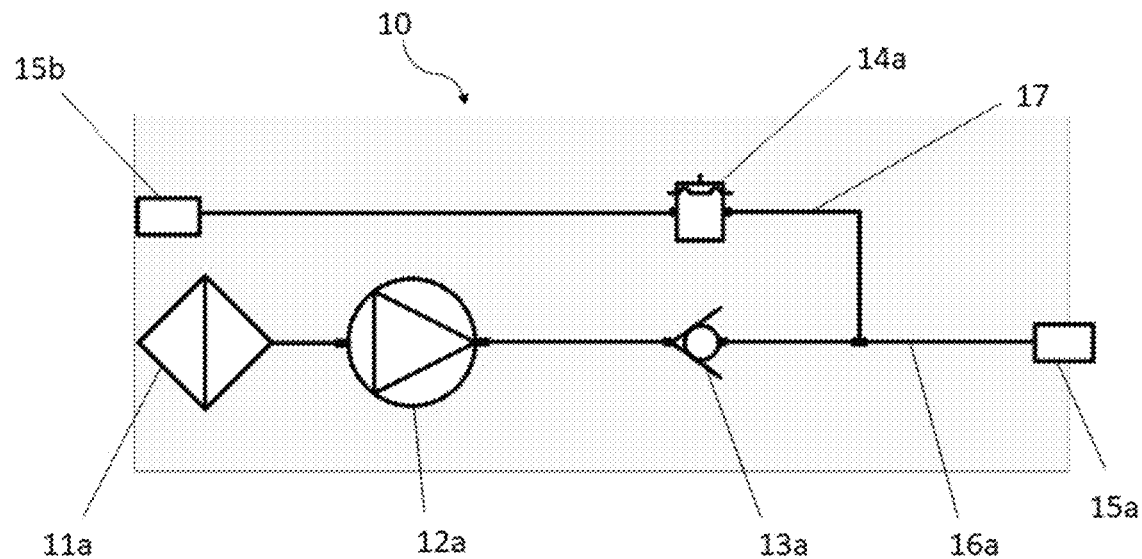
FIG. 9 shows a diagrammatic structure of an alternative embodiment of the ventilator according to the invention with the inspiratory airway with an open bypass with a separate apparatus output.

FIG. 9 shows a diagrammatic structure of an alternative embodiment of the ventilator 10 according to the invention with the inspiratory airway 16a with an open bypass 17 with a separate apparatus output 15b. The inspiratory airway 16a of the ventilator 10 comprises the apparatus input 11a and the apparatus output 15a. The breathing gas drive 12a, the non-return valve 13a and the switching valve 14a are arranged between the apparatus input 11a and the apparatus output 15a, wherein the switching valve 14a is arranged in the bypass 17. The bypass 17 is designed as an open bypass which comprises a separate apparatus output 15b. The open bypass 17 branches off from the inspiratory airway 16a between the non-return valve 13a and the apparatus output 15a, and opens in the separate apparatus output 15b. The breathing gas drive 12a is arranged between the apparatus input 11 and the non-return valve 13a. The switching valve 14a can be switched time-controlled, patient-triggered or based on a flow or volume of the breathing gas detected by a flowmeter. The flowmeter is arranged here between the separate apparatus output 15b and the switching valve 14a. In the event of a blockage of the inspiratory airway 16a, it is possible to discharge the breathing gas, discharged by the patient, through the switching valve 14a arranged in the open bypass 17, via the switching valve 14a. Through the arrangement of the non-return valve 13a between the breathing gas drive 12a and the apparatus output 15a, the non-return valve 13a is arranged on the pressure side of the ventilator 10.

Figure 10:
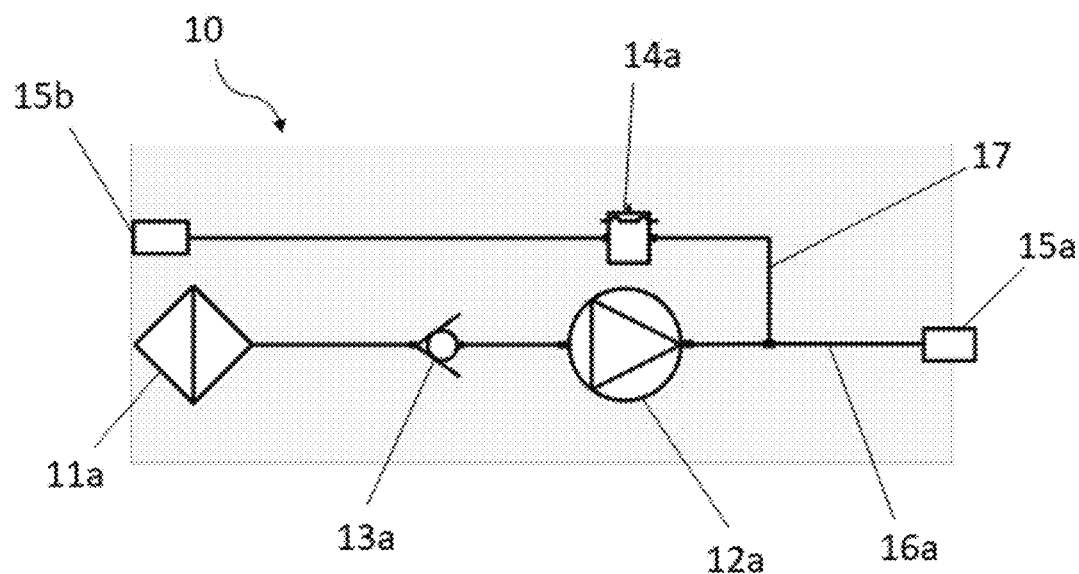
FIG. 10 shows a diagrammatic structure of an alternative embodiment of the ventilator according to the invention, shown in FIG. 9, with the inspiratory airway with the open bypass with the separate apparatus output.

FIG. 10 shows an alternative diagrammatic structure of an embodiment, shown in FIG. 9, of the ventilator 10 according to the invention with the inspiratory airway 16a and the open bypass 17 with the separate apparatus output 15b. The inspiratory airway 16a of the ventilator 10 then comprises the apparatus input 11a and the apparatus output 15a. The non-return valve 13a, the breathing gas drive 12a and the switching valve 14a are arranged between the apparatus input 11a and the apparatus output 15a, wherein the switching valve 14a is arranged in the bypass 17. The bypass 17 is formed as an open bypass which comprises a separate apparatus output 15b. The open bypass 17 branches off from the inspiratory airway 16a between the breathing gas drive 12a and the apparatus output 15a and opens in the separate apparatus output 15b. The breathing gas drive 12a is arranged between the non-return valve 13a and the apparatus output 15a. It is possible in the event of a blockage of the inspiratory airway 16a to discharge breathing gas discharged from the patient via the switching valve 14a through the switching valve 14a arranged in the open bypass 17. As a result of the open bypass 17 arranged between the breathing gas drive 12a and the apparatus output 15a, breathing gas can be returned without having to pass the breathing gas drive. As a result of arranging the non-return valve 13a between the apparatus input 11a and the breathing gas drive 12a, the non-return valve 13a is arranged on the suction side of the ventilator 10.

Figure 11:
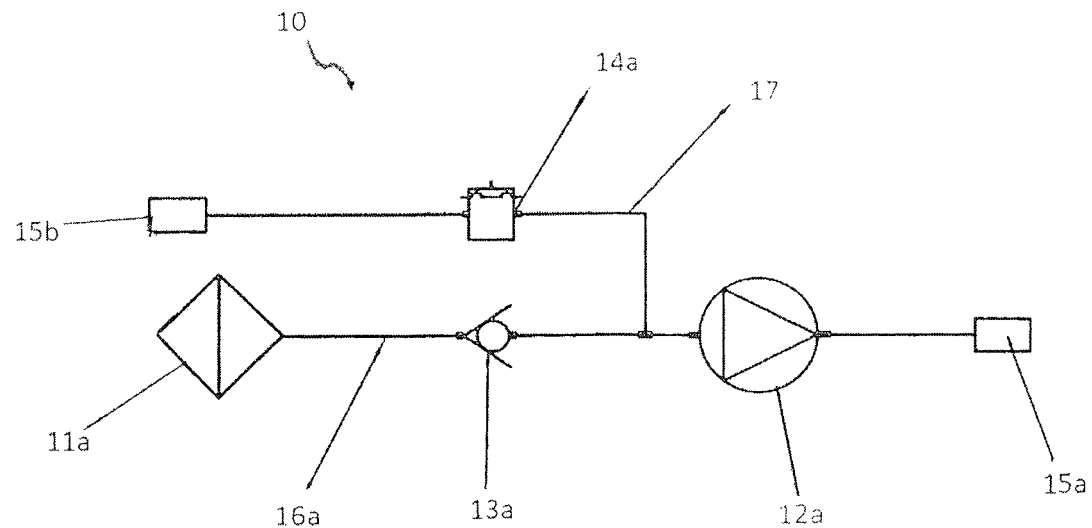
FIG. 11 shows a diagrammatic structure of an alternative embodiment of the ventilator according to the invention, shown in FIG. 9, with the inspiratory airway with the open bypass with the separate apparatus output.

FIG. 11 shows an alternative diagrammatic structure of an alternative embodiment, shown in FIGS. 9 and 10, of the ventilator 10 according to the invention with the inspiratory airway 16a and the open bypass 17 with the separate apparatus output 15b. The inspiratory airway 16a of the ventilator 10 comprises here the apparatus input 11a and the apparatus output 15a. The breathing gas drive 12a, the non-return valve 13 as well as the switching valve 14a are arranged between the apparatus input 11a and the apparatus output 15a, wherein the switching valve 14a is arranged in the bypass 17. The bypass 17 is designed as an open bypass which comprises a separate apparatus output 15b. The open bypass 17 branches off from the inspiratory airway 16a between the non-return valve 13a and the breathing gas drive 12a and opens in the separate apparatus output 15b. The breathing gas drive 12a is arranged between the non-return valve 13a and the apparatus output 15a. Through the switching valve 14a arranged in the open bypass 17 it is possible, in the event of a blockage in the inspiratory airway 16a, to discharge breathing gas discharged by the patient via the switching valve 14a. By arranging the non-return valve 13a between the apparatus input 11a and the breathing gas drive 12a, the non-return valve 13a is arranged on the suction side of the ventilator 10.

Figure 12:
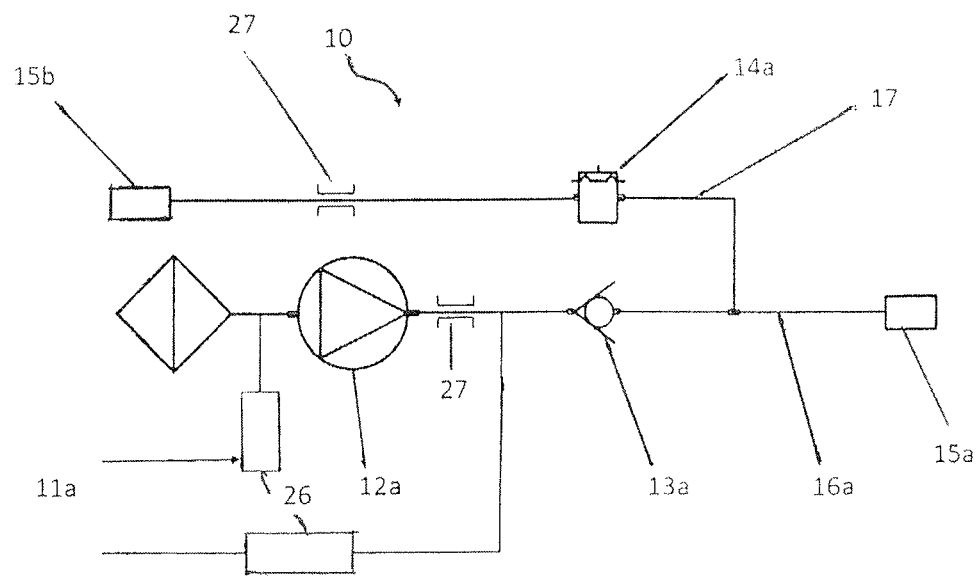
FIG. 12 shows a diagrammatic structure of an alternative embodiment of the ventilator according to the invention—shown in FIGS. 9 and 11—with the inspiratory airway with an open bypass with a separate apparatus output.

FIG. 12 shows a diagrammatic structure of an alternative embodiment of the ventilator 10 according to the invention with the inspiratory airway 16a with the open bypass 17 with the separate apparatus output 15b. The inspiratory airway 16a of the ventilator 10 comprises the apparatus input 11a and the apparatus output 15a. The breathing gas drive 12a, the non-return valve 13a, a flowmeter 27 as well as the switching valve 14a are arranged between the apparatus input 11a and the apparatus output 15a, wherein the switching valve 14a is arranged in the bypass 17. The bypass 17 is designed as an open bypass which comprises a separate apparatus output 15b as well as at least one flowmeter 27. The open bypass 17 branches off from the inspiratory airway 16a between the non-return valve 13a and the apparatus output 15a, and opens in the separate apparatus output 15b. The breathing gas drive 12a is arranged between the apparatus input 11a and the non-return valve 13a. The switching valve 14a can be switched time-controlled, patient-triggered or based on a flow or volume of the breathing gas detected by the flowmeter 27 arranged in the bypass 17. The flowmeter 27 in the bypass 17 is here arranged between the separate apparatus output 15b and the switching valve 14a. Through the switching valve 14a arranged in the open bypass 17 it is possible in the event of a blockage of the inspiratory airway 16a to discharge breathing gas discharged by the patient through the switching valve 14a. Through the arrangement of the non-return valve 13a between the breathing gas drive 12a and the apparatus output 15a, the non-return valve 13a is arranged on the pressure side of the ventilator 10.

The embodiment illustrated in FIG. 12 further shows that the inspiratory airway 16a comprises additionally at least one further valve 26 which is set up to ensure a supply of oxygen or air or compressed air to the inspiratory airway 16a. The inspiratory airway 16a moreover comprises at least one flowmeter 27 wherein the flowmeter 27 is arranged between the breathing gas drive 12a and the non-return valve 13a. The further valve 26 can open into the inspiratory airway 16a between the apparatus input 11a and the breathing gas drive 12a as well as between the flowmeter 27 and the non-return valve 13a. The further valve 26 is as a rule a proportional valve.

With the embodiment shown in FIG. 12 the region (inspiratory unit) of the open bypass 17 with the switching valve 14a, the flowmeter 27 and the separate apparatus output 15b, as well as the region of the inspiratory airway 16a with the non-return valve 13a and the apparatus output 15a can be removed from the ventilator and autoclaved. The region of the inspiratory airway 16a with the apparatus input 11a, the breathing gas drive 12a and the flowmeter 27 is set up and designed so that it cannot come into contact with contaminated breathing gas.

The alternative embodiments of the ventilator 10 shown in FIGS. 9 to 11 can optionally each comprise a flowmeter which detects a flow or volume or a pressure of the breathing gas in the airway.

The switching valve 14a in the alternative embodiments, such as shown in FIGS. 9 to 11, can optionally be switched based on the flow or volume detected by the flowmeter.

The alternative embodiments shown in FIGS. 9 to 11 can optionally be combined with the embodiments shown in FIGS. 1 to 8. Alternatively, the open bypass 17 shown in FIGS. 9 to 11 can replace the closed bypass 17 in the embodiments shown in FIGS. 1 to 8.

REFERENCE NUMERAL LIST

10 Ventilator
11a Apparatus input
11b Second, separate apparatus input
12a Breathing gas drive
12b Breathing gas drive
13a Non-return valve
13b Non-return valve
14a Switching valve
14b Switching valve
14c Switching valve
14d Switching valve
15a Apparatus output
15b Separate apparatus output
16a First airway
16b Second airway
16c Airway, for the expiratory breathing gas flow
16d Separate expiratory airway
17 Bypass
18a Flowmeter
18b Flowmeter
18c Flowmeter
18d Flowmeter
19 Tube system
20 Patient interface
21 Expiratory apparatus input
22a Expiratory apparatus output
22b Expiratory apparatus output
23 Tube system
24 First branch
25 Second branch
26 Further valves, proportional valves
27 Further flowmeters

What is claimed is:

1. A ventilator, wherein the ventilator comprises at least an apparatus input and an apparatus output and an airway between the apparatus input and the apparatus output, the airway comprising at least one inspiratory airway and at least one expiratory airway, a breathing gas drive, a non-return valve and at least one switching valve being arranged in the airway, the non-return valve being arranged in the at least one inspiratory airway and configured to prevent a flow of breathing gas in a direction from the apparatus output to the apparatus input and the at least one switching valve being configured to discharge expiratory gas of a patient via the at least one inspiratory airway in the event of a blockage/obstruction of the at least one expiratory airway and to at least temporarily enable a flow of breathing gas in a direction from the apparatus output to the apparatus input or to a separate apparatus opening.

2. The ventilator of claim 1, wherein a flowmeter is arranged between the non-return valve and the apparatus output.

3. The ventilator of claim 1, wherein the at least one switching valve is arranged in a bypass around the non-return valve.

4. The ventilator of claim 1, wherein the at least one switching valve forms a bypass around the non-return valve.

5. The ventilator of claim 1, wherein the at least one switching valve is set up to open and/or close a bypass, the at least one switching valve being configured so that it can be switched automatically or actively.

6. The ventilator of claim 1, wherein the breathing gas drive is arranged between the apparatus input and the non-return valve and is configured to convey breathing gas in a direction of the non-return valve and the apparatus output.

7. The ventilator of claim 1, wherein a bypass branches off to the at least one switching valve between the breathing gas drive and the non-return valve and opens back again into the airway between the non-return valve and the apparatus output.

8. The ventilator of claim 1, wherein the breathing gas drive is arranged between the non-return valve and the apparatus output, and is configured to convey breathing gas in a direction of the apparatus output.

9. The ventilator of claim 1, wherein a bypass branches off to the at least one switching valve between the apparatus input and the non-return valve and opens back again into the airway between the non-return valve and the breathing gas drive.

10. The ventilator of claim 1, wherein in addition to a bypass a second airway is formed which comprises a second apparatus input and at least one further non-return valve and opens into the first airway before the common apparatus output.

11. The ventilator of claim 1, wherein an additional airway is formed for an expiratory breathing gas flow and comprises an expiratory apparatus input and an expiratory apparatus output.

12. The ventilator of claim 11, wherein the additional airway leads from the expiratory apparatus input to the expiratory apparatus output, an additional switching valve and a flowmeter being arranged in the additional airway.

13. The ventilator of claim 12, wherein between the expiratory apparatus input and the additional switching valve a separate expiratory airway comprising a further switching valve and a further flowmeter leads to a separate apparatus output.

14. The ventilator of claim 11, wherein a tube system is adapted to the apparatus output and runs with a first branch to a patient interface and, before the patient interface, runs with a second branch to the expiratory apparatus input for expiratory breathing gas.

15. The ventilator of claim 1, wherein the at least one switching valve is arranged in a bypass around the non-return valve and the bypass branches off to the at least one switching valve between the breathing gas drive and the non-return valve, and opens back again into the airway between the non-return valve and the apparatus output.

16. A ventilator, wherein the ventilator comprises an apparatus input and an apparatus output and an airway between the apparatus input and the apparatus output, the airway comprising at least one inspiratory airway and at least one expiratory airway, a breathing gas drive, a non-return valve and a switching valve, the non-return valve being arranged in the at least one inspiratory airway and configured to prevent a flow of breathing gas in a direction from the apparatus output to the apparatus input and the at least one switching valve being configured to discharge expiratory gas of a patient via the at least one inspiratory airway in the event of a blockage/obstruction of the at least one expiratory airway and to at least temporarily enable a flow of breathing gas in a direction from the apparatus output to the apparatus input or to a separate apparatus opening, and wherein (i) the ventilator further comprises a second inspiratory airway which comprises a separate apparatus input and a further non-return valve, the second inspiratory airway being set up to draw breathing gas in through the separate apparatus input and convey it in a direction of the apparatus output, or (ii) the switching valve is arranged in a bypass, the bypass being formed as an open bypass which comprises a separate apparatus output, the open bypass branching off from the inspiratory airway between the non-return valve and the apparatus output and opening in a separate apparatus output, the inspiratory airway comprising at least one further valve and a flowmeter, the flowmeter being arranged between the breathing gas drive and a further non-return valve.

17. The ventilator of claim 16, wherein the switching valve is arranged in a bypass, the bypass being formed as an open bypass which comprises a separate apparatus output, the open bypass branching off from the inspiratory airway between the non-return valve and the apparatus output and opening in a separate apparatus output, the inspiratory airway comprising at least one further valve and a flowmeter, the flowmeter being arranged between the breathing gas drive and a further non-return valve.

18. A ventilator, wherein the ventilator comprises an apparatus input and an apparatus output and an airway between the apparatus input and the apparatus output, the airway comprising at least one inspiratory airway and at least one expiratory airway, a breathing gas drive, a non-return valve and a switching valve, the non-return valve being arranged in the at least one inspiratory airway and configured to prevent a flow of breathing gas in a direction from the apparatus output to the apparatus input and the at least one switching valve being configured to discharge expiratory gas of a patient via the at least one inspiratory airway in the event of a blockage/obstruction of the at least one expiratory airway and to at least temporarily enable a flow of breathing gas in a direction from the apparatus output to the apparatus input or to a separate apparatus opening, and wherein the switching valve is arranged in a bypass, the bypass being formed as an open bypass which comprises a separate apparatus output, and the open bypass branching off from the inspiratory airway between the non-return valve and the apparatus output and opening into the separate apparatus output.

19. The ventilator of claim 18, wherein the inspiratory airway further comprises at least one further valve.

20. The ventilator of claim 18, wherein the ventilator further comprises at least one flowmeter which is arranged in the open bypass.

* * * * *